United States Patent
Pastore et al.

(10) Patent No.: US 7,257,443 B2
(45) Date of Patent: Aug. 14, 2007

(54) METHOD AND APPARATUS FOR DETECTING OSCILLATIONS IN CARDIAC RHYTHM WITH ELECTROGRAM SIGNALS

(75) Inventors: Joseph M. Pastore, Minneapolis, MN (US); Steven D. Girouard, Woodbury, MN (US); Bruce H. KenKnight, Maple Grove, MN (US); Qingsheng Zhu, Little Canada, MN (US); Jiang Ding, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 192 days.

(21) Appl. No.: 11/184,325

(22) Filed: Jul. 19, 2005

(65) Prior Publication Data

US 2005/0256542 A1    Nov. 17, 2005

Related U.S. Application Data

(63) Continuation of application No. 10/106,836, filed on Mar. 26, 2002, now Pat. No. 6,957,105.

(51) Int. Cl.
*A61N 1/368* (2006.01)

(52) U.S. Cl. .............................. 607/9; 607/14; 607/15; 600/515; 600/516; 600/517

(58) Field of Classification Search .................... 607/9, 607/14, 15, 4, 5, 17, 62; 600/509, 515, 516, 600/517–519, 521, 526, 528
See application file for complete search history.

(56) References Cited

U.S. PATENT DOCUMENTS

| | | | |
|---|---|---|---|
| 4,354,497 A | 10/1982 | Kahn | |
| 4,549,548 A | 10/1985 | Wittkampf et al. | |
| 4,554,922 A | 11/1985 | Prystowsky et al. | |
| 4,628,934 A | 12/1986 | Pohndorf et al. | |
| 4,674,518 A | 6/1987 | Salo | |
| 4,686,987 A | 8/1987 | Salo et al. | |
| 4,872,459 A | 10/1989 | Pless et al. | |
| 4,880,005 A | 11/1989 | Pless et al. | |
| 4,928,688 A | 5/1990 | Mower | |
| 5,058,605 A | 10/1991 | Slovak | |
| 5,137,019 A | 8/1992 | Pederson et al. | |

(Continued)

FOREIGN PATENT DOCUMENTS

EP    0522693    1/1993

(Continued)

OTHER PUBLICATIONS

Hada, Yoshiyuki, et al., "Pulsus alternans determined by biventricular simultaneous systolic time intervals", *Circulation*, 65(3), (Mar. 1982), 617-26.

(Continued)

*Primary Examiner*—Kennedy Schaetzle
(74) *Attorney, Agent, or Firm*—Schwegman, Lundberg, Woessner, & Kluth, P.A.

(57) ABSTRACT

A cardiac rhythm management device is configured to detect oscillations in cardiac rhythm by comparing electrogram signals during successive heart beats. Upon detection of electrical alternans, the device may adjust its operating behavior to compensate for the deleterious effects of the condition.

20 Claims, 3 Drawing Sheets

U.S. PATENT DOCUMENTS

| | | |
|---|---|---|
| 5,156,149 A | 10/1992 | Hudrlik |
| 5,174,289 A | 12/1992 | Cohen |
| 5,190,035 A | 3/1993 | Salo et al. |
| 5,233,985 A | 8/1993 | Hudrlik |
| 5,267,560 A | 12/1993 | Cohen |
| 5,284,136 A | 2/1994 | Hauck et al. |
| 5,334,222 A | 8/1994 | Salo et al. |
| 5,370,665 A | 12/1994 | Hudrlik |
| 5,391,190 A | 2/1995 | Pederson et al. |
| 5,417,717 A | 5/1995 | Salo et al. |
| 5,487,752 A | 1/1996 | Salo et al. |
| 5,514,161 A | 5/1996 | Limousin |
| 5,584,867 A | 12/1996 | Limousin et al. |
| 5,584,868 A | 12/1996 | Salo et al. |
| 5,674,259 A | 10/1997 | Gray |
| 5,792,203 A | 8/1998 | Schroeppel |
| 5,797,970 A | 8/1998 | Pouvreau |
| 5,836,974 A | 11/1998 | Christini et al. |
| 5,935,160 A | 8/1999 | Auricchio et al. |
| 5,995,871 A | 11/1999 | Knisley |
| 6,022,322 A | 2/2000 | Prutchi |
| 6,038,483 A | 3/2000 | KenKnight et al. |
| 6,058,328 A | 5/2000 | Levine et al. |
| 6,058,329 A | 5/2000 | Salo et al. |
| 6,112,117 A | 8/2000 | KenKnight et al. |
| 6,151,524 A | 11/2000 | Krig et al. |
| 6,161,042 A | 12/2000 | Hartley et al. |
| 6,223,082 B1 | 4/2001 | Bakels et al. |
| 6,253,107 B1 | 6/2001 | Albrecht et al. |
| 6,272,377 B1 | 8/2001 | Sweeney et al. |
| 6,273,377 B1 | 8/2001 | Archer et al. |
| 6,278,894 B1 | 8/2001 | Salo et al. |
| 6,285,898 B1 | 9/2001 | Ben-Haim |
| 6,292,694 B1 | 9/2001 | Schloss et al. |
| 6,361,522 B1 | 3/2002 | Scheiner et al. |
| 6,363,279 B1 | 3/2002 | Ben-Haim et al. |
| 6,370,424 B1 | 4/2002 | Prutchi |
| 6,453,191 B2 | 9/2002 | Krishnamachari |
| 2003/0023278 A1 | 1/2003 | Pastore et al. |
| 2003/0208240 A1 | 11/2003 | Pastore et al. |
| 2003/0233132 A1 | 12/2003 | Pastore et al. |
| 2004/0054381 A1 | 3/2004 | Pastore et al. |

FOREIGN PATENT DOCUMENTS

| | | |
|---|---|---|
| WO | WO-97/25098 | 7/1997 |
| WO | WO-00/04947 | 2/2000 |
| WO | WO-00/09206 | 2/2000 |
| WO | WO-01/08748 | 2/2001 |
| WO | WO-01/30436 | 5/2001 |

OTHER PUBLICATIONS

Konta, Tsuyoshi, et al., "Significance of Discordant ST Alternans in Ventricular Fibrillation", *Circulation*, 82(6), (Dec. 1990),2185-2189.

Lee, Y. C., et al., "Pulsus alternans in patients with congestive cardiomyopathy", *Circulation*, 65(7), (Jun. 1982), 1533-4.

Rubenstein, Donald S., et al., "Premature Beats Elicit a Phase Reversal of Mechanoelectrical Alternans in Cat Ventricular Myocytes", *Circulation*, vol. 91, No. 1, Jan. 1995, American Heart Association,(Jan. 1, 1995),201-214.

Schaefer, Saul, et al., "Clinical and hemodynamic characteristics of patients with inducible pulsus alternans", *American Heart Journal*, vol. 115, No. 6, (Jun. 1988),1251-7.

Smith, Damon, et al., "Influence of the Aortic Component of the Second Heart Sound on Left Ventricular Maximal Negative dP/dt in the Dog", *Am. J. Cardiol.*, 55: 205, (1985),205-209.

METHOD AND APPARATUS FOR DETECTING OSCILLATIONS IN CARDIAC RHYTHM WITH ELECTROGRAM SIGNALS

CROSS-REFERENCE TO RELATED APPLICATION

This application is a continuation of U.S. patent application Ser. No. 10/106,836, now U.S. Pat. No. 6,957,105, filed on Mar. 26, 2002, the specification of which is incorporated herein by reference.

FIELD OF THE INVENTION

This patent application pertains to methods and apparatus for cardiac rhythm management. In particular, it relates to the detections of oscillations in heart rhythm and its use by a cardiac rhythm management device.

BACKGROUND

Cardiac rhythm refers to the temporal pattern of electrical or mechanical activity in the heart. Cardiac rhythm management devices are implantable devices that provide electrical stimulation to selected chambers of the heart in order to treat disorders of cardiac rhythm. An implantable pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Cardiac rhythm management devices may also be used to treat tachyarrhythmias where the heart rhythm is too fast. In a type of pacing therapy called anti-tachycardia pacing, one or more pacing pulses are output during a cardiac cycle in an effort to interrupt the reentrant circuit causing a tachycardia. Other tachyarrhythmias such as fibrillation can be treated by devices that deliver a cardioversion/defibrillation shock when the tachyarrhythmia is detected.

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Heart failure refers to a clinical syndrome in which an abnormality of cardiac function causes a below normal cardiac output that can fall below a level adequate to meet the metabolic demand of peripheral tissues. It usually presents as congestive heart failure (CHF) due to the accompanying venous and pulmonary congestion. Heart failure can be due to a variety of etiologies with ischemic heart disease being the most common. Some heart failure patients suffer from some degree of AV block or are chronotropically deficient such that their cardiac output can be improved with conventional bradycardia pacing. Such pacing, however, may result in some degree of uncoordination in atrial and/or ventricular contractions because pacing excitation from a single pacing site spreads throughout the myocardium via the conducting muscle fibers of either the atria or the ventricles, and not the faster specialized conduction pathways as in a physiological heart beat. Most pacemaker patients can still maintain more than adequate cardiac output with artificial pacing, but the diminishment in cardiac output may be significant in a heart failure patient whose cardiac output is already compromised. Intraventricular and/or interventricular conduction defects are also commonly found in heart failure patients and can contribute to cardiac dysfunction by causing unsynchronized contractions during intrinsic beats. In order to treat these problems, cardiac rhythm management devices have been developed that provide electrical pacing stimulation to one or more heart chambers in an attempt to improve the coordination of atrial and/or ventricular contractions, termed cardiac resynchronization therapy.

SUMMARY OF THE INVENTION

The present invention relates to an implantable cardiac rhythm management device that is configured to detect oscillatory behavior in the electrical rhythm of the heart, referred to as electrical alternans. Since electrical alternans is known to be potentially arrhythmogenic, the device may be further configured to adjust its operation when the condition is detected. Such operation adjustments may relate to the manner in which either bradycardia pacing or anti-tachycardia pacing is delivered. Electrical alternans is also highly correlated with systolic dysfunction of the heart. A cardiac rhythm management device may therefore also be configured to compensate for the decrease in cardiac output when electrical alternans is detected by initiating or modifying the delivery of cardiac resynchronization therapy.

DETAILED DESCRIPTION

Figure 1:
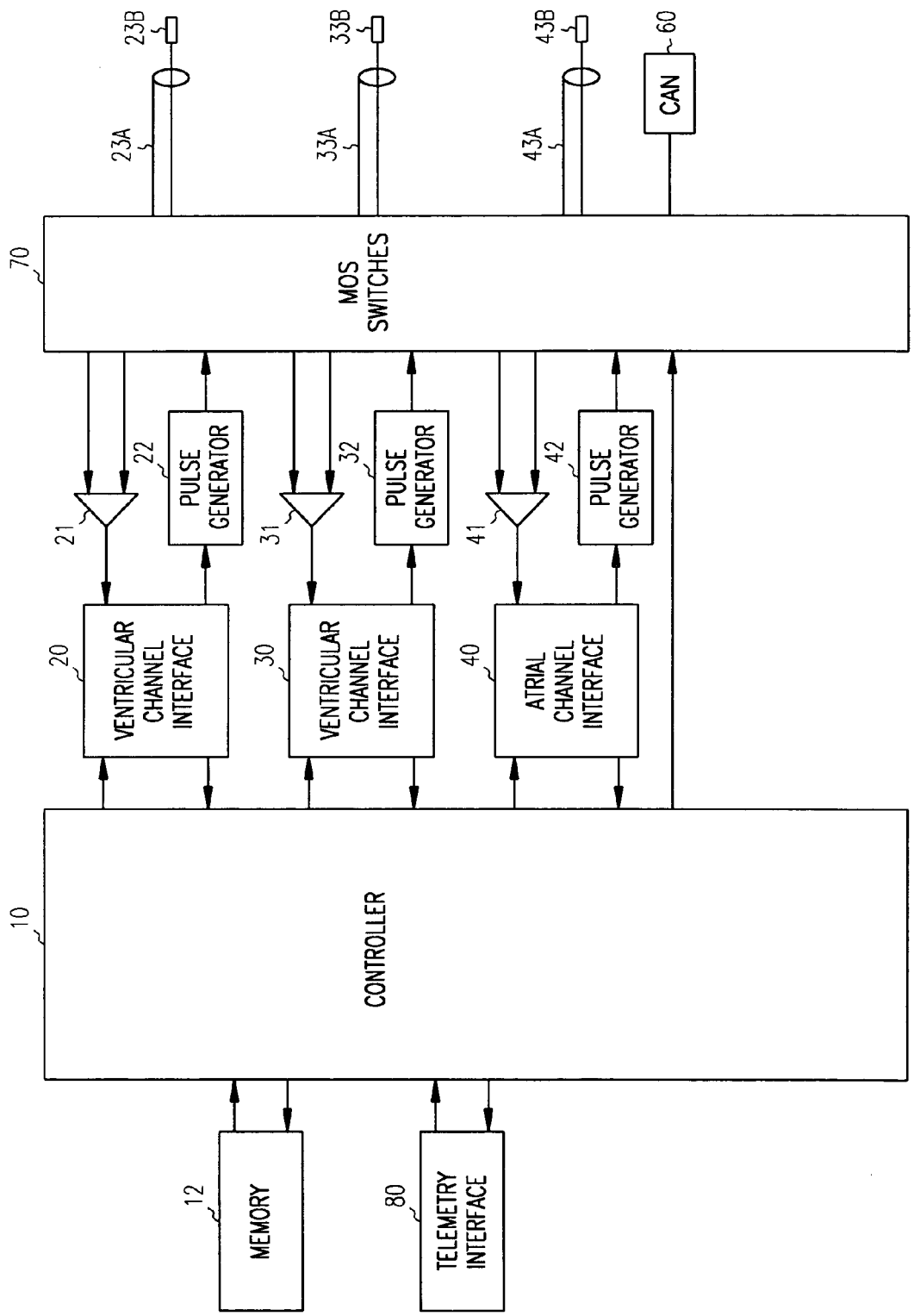
FIG. 1 is a system diagram of an exemplary cardiac rhythm management device.

Under certain circumstances, the pattern of electrical excitation of the human heart exhibits oscillations during successive heart beats. Such beat-to-beat oscillations may relate to the amplitude, duration, and/or morphology of myocardial action potentials as well as of externally recorded waveforms (e.g., an EKG) that reflect the depolarization and repolarization of the myocardium during a heart beat. This phenomena is referred to as electrical alternans and is usually indicative of a pathological state in which potentially dangerous cardiac arrhythmias are more likely to occur. In one of its aspects, the present invention provides an implantable cardiac rhythm management device that is configured to utilize its sensing channels to detect electrical alternans and then to adjust its operation accordingly. The sensing channels produce electrogram signals that reflect the electrical activity at a local cardiac site near which a sensing electrode is disposed, and such local electrical activity exhibits oscillations during electrical alternans. In one embodiment, the device detects the start of depolarization and the end of repolarization (i.e., corresponding to the Q wave and T wave, respectively, in a surface EKG) in an electrogram signal from a ventricular sensing channel and measures the time interval therebetween. The interval so measured corresponds to the action potential duration of the local cardiac site. The device may then detect the presence of electrical alternans when the difference between intervals measured during successive heart beats exceeds a specified threshold value and the difference persists for a specified length of time or number of beats. Other embodiments may process the electrogram signal to determine if oscillations exist with respect to other features such as amplitude or waveform morphology and then detect electrical alternans if the oscillations are of sufficient magnitude and duration. Electrical alternans may also be detected by processing of electrogram signals from atrial sensing channels.

As aforesaid, the presence of electrical alternans in an individual may indicate that an arrhythmogenic condition exists, and it may be deleterious for an implantable cardiac rhythm management device to deliver its therapy to the patient in a normal manner under such circumstances. In accordance with the invention, an implantable cardiac rhythm management device that detects electrical alternans in the manner described above is also configured to adjust its operating behavior when alternans is detected. Such a device may deliver any kind of cardiac rhythm management therapy to the patient during normal conditions including bradycardia pacing, anti-tachycardia pacing, and/or cardioversion/defibrillation. Since it is known that electrical alternans occurs above a critical threshold heart rate, for example, bradycardia pacing at a rate above that critical threshold when electrical alternans is present may aggravate the situation. In one embodiment, a device configured to deliver bradycardia pacing adjusts its pacing rate to a lower value when electrical alternans is detected. Rapid heart rates may also more readily trigger arrhythmias when an arrhythmogenic condition such as electrical alternans is present. In another embodiment, a device configured to deliver anti-tachycardia pacing lowers the threshold heart rate at which such therapy is initiated when electrical alternans is detected in order to reduce the probability of an arrhythmia occurring.

Electrical alternans is also highly correlated to oscillations in the mechanical function of the heart that result in alternations in pulse pressure, referred to as pulsus alternans. Pulsus alternans is generally taken by clinicians to indicate systolic dysfunction, particularly in the left ventricle. Since the pumping action of the heart is due to the electromechanical coupling between electrical depolarization of myocardial cells and their mechanical contraction, electrical alternans and pulsus alternans may be different manifestations of the same underlying phenomena in certain cases. In any event, detection of electrical alternans means that it is highly probable that pulsus alternans is also present. As noted above, certain cardiac rhythm management devices are designed to deliver pacing therapy in a manner that improves the coordination of both ventricles (or both atria) during systolic contractions, termed cardiac resynchronization therapy. The presence of pulsus alternans in such patients indicates that systolic function has been further impaired, and it may be beneficial for a device configurable for delivering resynchronization pacing to adjust its operating parameters to compensate for this when electrical alternans, serving as a surrogate for pulsus alternans, is detected. For example, a device may be configured to deliver bradycardia pacing to one ventricle in a conventional manner or even no pacing under normal conditions. If electrical alternans is detected, however, the device may be programmed to initiate resynchronization therapy by pacing both ventricles or one ventricle at multiple sites. In another embodiment, a device configured to deliver resynchronization pacing during normal conditions may adjust one or more operating parameters when electrical alternans is detected so that the resynchronization pacing is modified. Examples of operating parameters that may be so adjusted are the biventricular delay interval between paces delivered to the right and left ventricles and the atrio-ventricular delay interval between an atrial pace or intrinsic sense and a subsequent ventricular pace.

1. Exemplary Hardware Platform

Cardiac rhythm management devices are usually implanted subcutaneously or submuscularly on a patient's chest and have leads threaded intravenously into the heart to connect the device to electrodes used for sensing and pacing. Leads may also be positioned on the epicardium by various means. A block diagram of a multi-site pacemaker having three sensing/pacing channels is shown in FIG. 1. (As the term is used herein, a "pacemaker" should be taken to mean any cardiac rhythm management device, such as an implantable cardioverter/defibrillator, with a pacing functionality.) Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber. The controller of the pacemaker is made up of a microprocessor 10 communicating with a memory 12 via a bidirectional data bus, where the memory 12 comprises a ROM (read-only memory) for program storage and a RAM (random-access memory) for data storage. The controller can be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry interface 80 is also provided for communicating with an external programmer.

The multiple sensing/pacing channels may be configured to deliver bradycardia pacing, cardiac resynchronization therapy, or anti-tachycardia pacing. Illustrated in FIG. 1 is a configuration with one atrial and two ventricular sensing/pacing channels for delivering biventricular pacing. The atrial sensing/pacing channel in FIG. 1 comprises ring electrode 43a, tip electrode 43b, sense amplifier 41, pulse generator 42, and an atrial channel interface 40 which communicates bidirectionally with the controller 10. The device also has two ventricular sensing/pacing channels that similarly include ring electrodes 23a and 33b, tip electrodes 23b and 33b, sense amplifiers 21 and 31, pulse generators 22 and 32, and ventricular channel interfaces 20 and 30. Each channel thus includes a pacing channel made up of the pulse generator connected to the electrode and a sensing channel made up of the sense amplifier connected to the electrode. The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or changing the pacing pulse amplitude. For each channel, the same electrode pair is used for both sensing and pacing. In this embodiment, bipolar leads that include two electrodes are used for outputting a pacing pulse and/or sensing intrinsic activity. Other embodiments may employ a single electrode for sensing and pacing in each channel, known as a unipolar lead. A MOS switching network 70 controlled by the microprocessor is used to switch the electrodes from the input of a sense amplifier to the output of a pulse generator.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The time intervals between such senses can also be measured in order to detect tachyarrhythmias so that appropriate therapy can be delivered by the device. As described below, the controller may also be programmed to detect electrical alternans and to adjust the manner in which pacing therapy is delivered by the device upon such detection.

2. Detection of Electrical Alternans

Figure 2A:
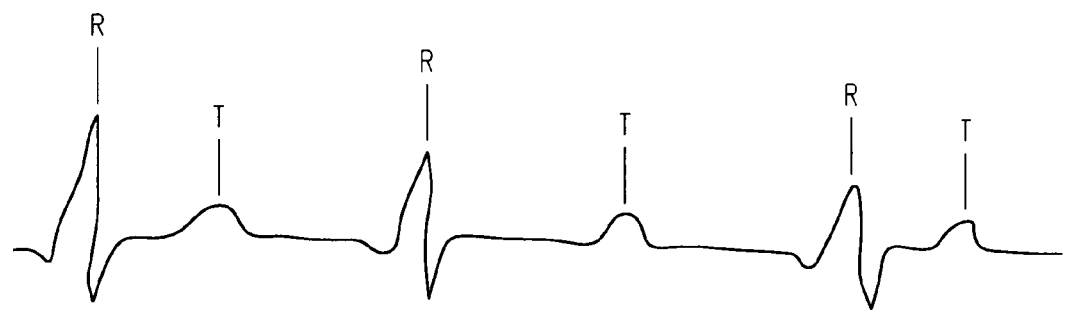
FIGS. 2A and 2B are exemplary electrogram waveforms that exhibit electrical alternans.
Figure 2B:
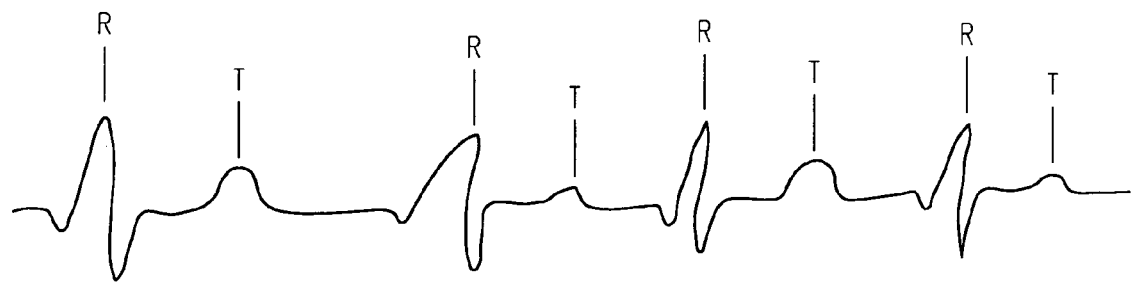

FIGS. 2A and 2B show examples of electrogram waveforms that exhibit electrical alternans. In FIG. 2A, the start of ventricular depolarization and the start of ventricular repolarization are marked by an R wave and T wave, respectively. The interval between the R wave and T wave during a single cardiac cycle then corresponds to the action potential duration in the myocardial fibers at the electrode site. One manifestation of electrical alternans is a beat-to-beat oscillation in the action potential duration as reflected by the successive differences in the R-T interval. FIG. 2B shows another example of an electrogram waveform in which the amplitude of the T wave oscillates from beat to beat.

In order to detect electrical alternans, the controller is programmed to extract some feature from the electrogram waveform during successive cardiac cycles and determine if a beat-to-beat oscillation exists with respect to that feature. Examples of such features include the R-T interval and T wave amplitude as noted above. In order to detect electrical alternans with specificity, specified threshold values may be employed so that the magnitude of the beat-to-beat oscillation must be of a certain magnitude and must persist for a certain number of heart beats or period of time before electrical alternans is detected.

Figure 3:
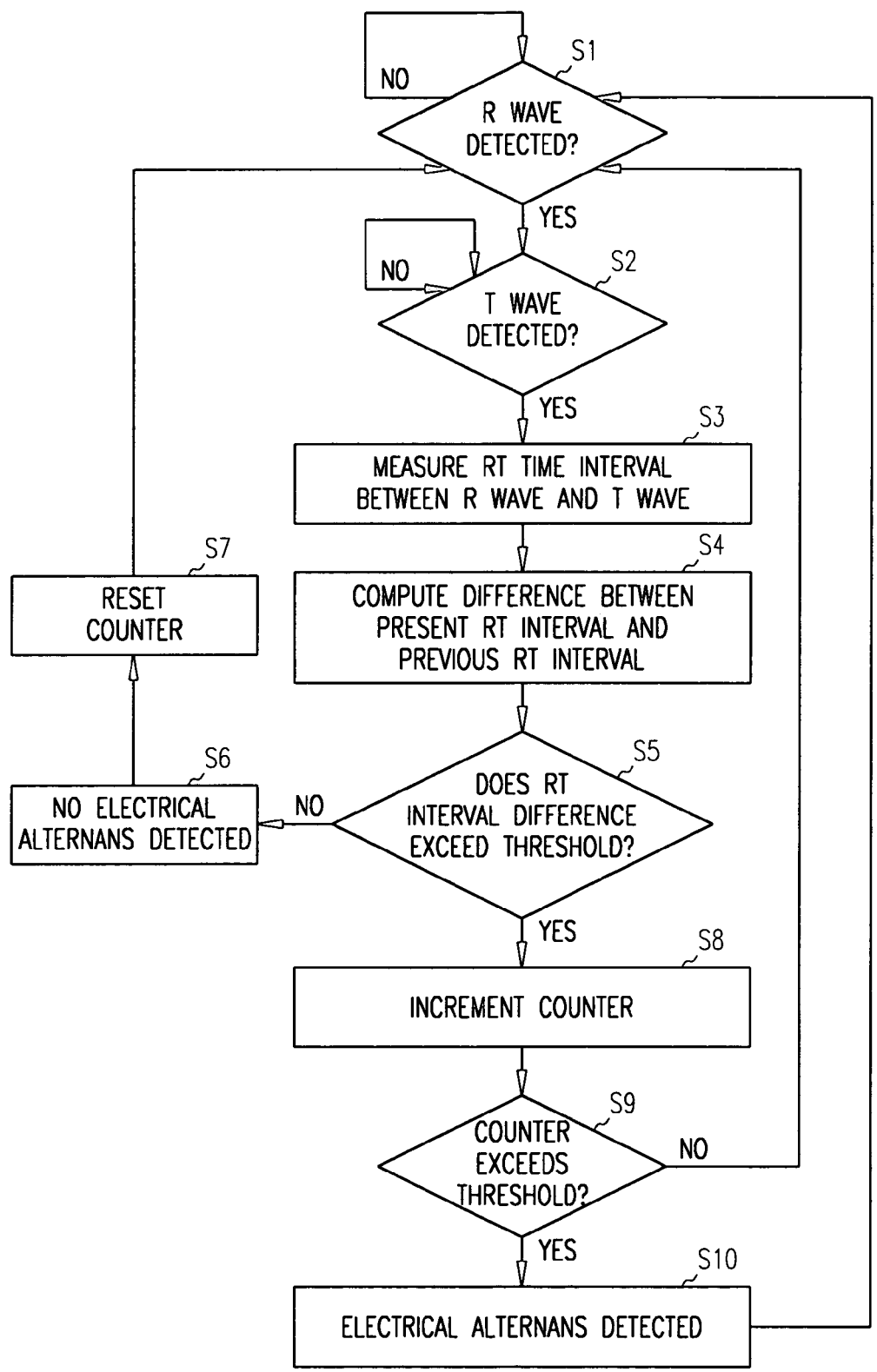
FIG. 3 illustrates an exemplary implementation of an algorithm for detecting electrical alternans.

FIG. 3 shows an exemplary algorithm for detecting electrical alternans based upon measurement of the R-T interval that can be implemented by the controller. At step S1, the device waits for an R wave (i.e., a ventricular sense). When an R wave is detected, the device then looks for a T wave in the ventricular sensing channel during an appropriate time window at step S2. When both R and T waves are detected during a cardiac cycle, the time interval between the two is measured at step S3. The difference between the R-T interval of the present cardiac cycle and the R-T interval of the previous cardiac cycle is then computed at step S4. If the R-T interval difference exceeds a specified threshold, as determined at step S5, a counter that keeps track of the number of consecutive R-T interval differences that exceed the threshold is incremented at step S8. Otherwise, a condition of no electrical alternans is detected at step S6, the counter is reset at step S7, and the device waits for the next R wave at step S1. If the R-T interval difference does exceed the threshold, after incrementing the counter at step S8, the counter's value is compared to a threshold count value at step S9. The threshold count value specifies the number of consecutive heart beats that the R-T interval difference must be above threshold before electrical alternans is detected. If the count exceeds the count threshold value, electrical alternans is detected at step S10. The device then returns to step S1 and measures the next R-T interval.

3. Adjustment of Bradycardia Pacing Rate

Bradycardia pacing modes refer to pacing algorithms used to pace the atria and/or ventricles when the intrinsic atrial and/or ventricular rate is inadequate due to, for example, AV conduction blocks or sinus node dysfunction. Such modes may either be single-chamber pacing, where either an atrium or a ventricle is paced, or dual-chamber pacing in which both an atrium and a ventricle are paced. Modern pacemakers are typically programmable so that they can operate in any mode which the physical configuration of the device will allow. Additional sensing of physiological data allows some pacemakers to change the rate at which they pace the heart in accordance with some parameter correlated to metabolic demand, called rate-adaptive pacing. Measurement of minute ventilation or body activity can be used to estimate metabolic demand for this purpose.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking and/or atrio-ventricular sequential pacing, another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing and atrio-ventricular sequential pacing attempt to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body. A pacemaker can also be configured to pace the atria on an inhibited demand basis, where an atrial escape interval is then defined as the maximum time interval in which an atrial sense must be detected after a ventricular sense or pace before an atrial pace will be delivered. The LRL in that case is the sum of the atrial escape interval and the AVI.

Electrical alternans is known to occur only above a certain critical threshold heart rate that varies with the individual patient. A pacemaker operating in an inhibited demand mode, by enforcing a specified minimum heart rate, can be responsible in some cases for maintaining a heart rate that allows electrical alternans to occur. The controller may therefore be programmed to decrease the LRL by a specified amount upon detection of electrical alternans. Such a decrease in the LRL may also be beneficial even if the electrical alternans persists by making the triggering of an arrhythmia less likely.

4. Adjustment of Anti-Tachycardia Pacing

The cardiac rhythm management device of FIG. 1 may be programmed with a plurality of selectable ATP pacing protocols that define the manner in which anti-tachycardia pacing is delivered. In a microprocessor-based device, the output of pacing pulses is controlled by a pacing routine that implements the selected pacing protocol as defined by various parameters. A data structure stored in memory contains the parameter sets that define each of the available pacing protocols. Pacing protocols for ATP therapy can generally be divided into two classes: those that deliver one or more pulses in timed relation to detected depolarizations and those that deliver a continuous pulse train for a specified time beginning after a detected depolarization. Both types of ATP protocols attempt to block the reentrant depolarization wavefront causing the tachycardia with a second depolarizing wavefront produced by a pacing pulse. Protocols of the first group may vary according to parameters that define the number of pulses delivered and the particular timing employed. Protocols of the second group include so-called burst pacing in which a short train of pulses is delivered for a specified time and may vary according to parameters that define the duration, frequency, and timing of the pulses.

The device delivers ATP therapy or a defibrillation shock under programmed control of the microprocessor in response to sensed activity from the sensing channels. A sensing routine analyzes the electrical activity received from the sensing channels in order to detect a tachyarrhythmia, and the tachyarrhythmia is then classified as a tachycardia (i.e., a terminable tachyarrhythmia) or fibrillation based upon rate and/or other criteria. The device detects a ventricular tachyarrhythmia, for example, by counting ventricular senses received via the ventricular sensing channel in order to measure the heart rate and determine whether the rate exceeds a selected threshold value. Once a tachyarrhythmia is detected, the rhythm is classified into either a tachycardia or a fibrillation zone by comparing the heart rate to a fibrillation rate boundary or by other means such as assessing the stability of the rhythm. If the tachyarrhythmia is classified as terminable, a pacing routine executed by the microprocessor delivers ATP pulses in accordance with the parameters of a selected protocol.

As noted above, the object of anti-tachycardia pacing is to create a pace-induced wavefront that propagates into the re-entrant circuit of the tachycardia and extinguishes it. Different protocols are apt to be more successful than others in terminating particular tachyarrhythmias that may differ as to rate and/or depolarization pattern. For this reason, modern cardiac rhythm management devices are capable of employing a number of different ATP protocols to deliver therapy where pacing parameters affecting the magnitude and timing of the pulses can also be adjusted for each protocol. Ideally, a clinician would program the device to deliver pacing therapy using a protocol and parameters that will perform best for a particular patient's tachyarrhythmia.

Upon detection of electrical alternans, the controller may be programmed to adjust the manner in which anti-tachycardia pacing is delivered that takes account of the greater potential for onset of an arrhythmic episode. In one example, the tachyarrhythmia rate threshold at which anti-tachycardia pacing is initiated is decreased so that the anti-tachycardia therapy is delivered sooner than in a normal mode of operation. Clinical testing of an individual patient may also reveal that certain anti-tachycardia pacing protocols are more successful than others in terminating a tachycardia preceded by electrical alternans but less successful in terminating a tachycardia not preceded by electrical alternans. In those cases, the controller can be programmed to adjust the particular anti-tachycardia pacing protocol to be used for terminating a tachycardia and/or particular parameters defining that protocol when electrical alternans is detected.

5. Adjustment of Cardiac Resynchronization Therapy

Cardiac resynchronization therapy is pacing stimulation applied to one or more heart chambers in a manner that restores or maintains synchronized contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. Resynchronization pacing, however, may also involve delivering paces to multiple sites of a heart chamber or pacing both ventricles and/or both atria in accordance with a resynchronization pacing mode as described below. Ventricular resynchronization pacing is useful in treating heart failure because, although not directly inotropic, resynchronization results in a more coordinated contraction of the ventricles with improved pumping efficiency and increased cardiac output. Resynchronization pacing of the atria may also be beneficial in certain heart failure patients, particularly for preventing the onset of atrial arrhythmias.

One way to deliver resynchronization therapy is to pace a site with a synchronous bradycardia pacing mode and then deliver one or more resynchronization paces to one or more additional pacing sites in a defined time relation to one or more selected sensing and pacing events that either reset escape intervals or trigger paces in the bradycardia pacing mode. One such resynchronization pacing mode may be termed offset resynchronization pacing. In this mode, a first site is paced with a bradycardia mode, and a second site receives a resynchronization pace at an offset interval with respect to the pace delivered to the first site. The offset interval may be zero in order to pace both sites simultaneously, positive in order to pace the first site after the second, or negative to pace the first site before the second. For example, in biventricular resynchronization pacing, one ventricle is paced with a bradycardia mode while the contralateral ventricle receives resynchronization paces at the specified biventricular offset interval. The offset interval would normally be individually specified to optimize cardiac output in a particular patient. Ventricular resynchronization can also be achieved in certain patients by pacing at a single unconventional site, such as the left ventricle instead of the right ventricle. In such a mode, right ventricular senses may be used to trigger left ventricular paces or used to define an escape interval that upon expiration causes delivery of a left ventricular pace.

Cardiac rhythm management devices for delivering resynchronization therapy may be configured in a number of different ways and with a number of different parameter settings. These parameters can be initially programmed after implantation while a physician is monitoring the patient so that the resynchronization therapy is delivered optimally. When the pumping efficiency of the patient's heart deteriorates as may be indicated by detection of an oscillatory rhythm, however, modification of those parameters may be necessary for continued optimal treatment. Accordingly, the controller may be programmed to modify its resynchronization pacing parameters upon detection of electrical alternans, with the exact manner in which such parameters are modified depending upon the individual patient's condition. Such parameter modifications may result in, for example, initiation of resynchronization pacing when such pacing is not normally delivered by the device, reconfiguration of pacing sites so that different cardiac sites are paced, adjustment of a biventricular offset interval for biventricular pacing modes, and adjustment of the atrio-ventricular interval for resynchronization pacing modes that employ atrial tracking or atrio-ventricular sequential pacing.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
   a sensing channel for generating an electrogram waveform;
   a controller programmed to extract a feature from the electrogram waveform during successive cardiac cycles and to detect electrical alternans by determining if a beat-to-beat oscillation above a specified threshold exists with respect to the extracted feature;
   pacing channels configurable for delivering cardiac resynchronization therapy;
   wherein the controller is programmed to either initiate or modify the delivery of cardiac resynchronization therapy if electrical alternans is detected.

2. The device of claim 1 wherein the extracted feature is an R-T interval.

3. The device of claim 1 wherein the extracted feature is a T-wave amplitude.

4. The device of claim 1 wherein the controller is programmed to deliver pacing therapy in accordance with a bradycardia mode, and further wherein the controller is programmed to decrease a programmed pacing rate when electrical alternans is detected.

5. The device of claim 1 wherein the controller is programmed to deliver anti-tachycardia pacing therapy when a measured heart rate exceeds a specified tachycardia threshold rate, and further wherein the controller is programmed to decrease the tachycardia threshold rate when electrical alternans is detected.

6. The device of claim 1 wherein the pacing channels are configurable for delivering atrial resynchronization pacing to both atria and further wherein the controller is programmed to either initiate or modify the delivery of atrial resynchronization therapy if electrical alternans is detected.

7. The device of claim 1 wherein the pacing channels are configurable for delivering ventricular resynchronization pacing to both ventricles and further wherein the controller is programmed to either initiate or modify the delivery of ventricular resynchronization therapy if electrical alternans is detected.

8. The device of claim 7 wherein the controller is programmed to adjust an atrio-ventricular delay interval for delivering ventricular resynchronization therapy if electrical alternans is detected.

9. The device of claim 7 wherein the controller is programmed to adjust a biventricular offset interval for delivering ventricular resynchronization therapy if electrical alternans is detected.

10. The device of claim 1 wherein the controller is programmed to reconfigure one or more pacing sites for delivering cardiac resynchronization therapy if electrical alternans is detected.

11. A method, comprising:
    generating an electrogram waveform;
    extracting a feature from the electrogram waveform during successive cardiac cycles and detecting electrical alternans by determining if a beat-to-beat oscillation above a specified threshold exists with respect to the extracted feature;
    initiating or modifying delivery of cardiac resynchronization therapy if electrical alternans is detected.

12. The method of claim 11 wherein the extracted feature is an R-T interval.

13. The method of claim 11 wherein the extracted feature is a T-wave amplitude.

14. The method of claim 11 further comprising delivering pacing therapy in accordance with a bradycardia mode and decreasing a programmed pacing rate when electrical alternans is detected.

15. The method of claim 11 further comprising delivering anti-tachycardia pacing therapy when a measured heart rate exceeds a specified tachycardia threshold rate and decreasing the tachycardia threshold rate when electrical alternans is detected.

16. The method of claim 11 further comprising delivering atrial resynchronization pacing to both atria and either initiating or modifying the delivery of atrial resynchronization therapy if electrical alternans is detected.

17. The method of claim 11 further comprising delivering ventricular resynchronization pacing to both ventricles and either initiating or modifying the delivery of ventricular resynchronization therapy if electrical alternans is detected.

18. The method of claim 17 further comprising adjusting an atrio-ventricular delay interval for delivering ventricular resynchronization therapy if electrical alternans is detected.

19. The method of claim 17 further comprising adjusting a biventricular offset interval for delivering ventricular resynchronization therapy if electrical alternans is detected.

20. The method of claim 11 further comprising reconfiguring one or more pacing sites for delivering cardiac resynchronization therapy if electrical alternans is detected.

* * * * *